(12) United States Patent
Lee

(10) Patent No.: US 8,361,793 B2
(45) Date of Patent: Jan. 29, 2013

(54) MONOCLONAL ANTIBODIES AGAINST GONADOTROPIN-RELEASING HORMONE RECEPTOR

(75) Inventor: Chi-Yu Gregory Lee, Vancouver (CA)

(73) Assignee: Vancouver Biotech Ltd., Vancouver (CA)

( * ) Notice: Subject to any disclaimer, the term of this patent is extended or adjusted under 35 U.S.C. 154(b) by 0 days.

(21) Appl. No.: 13/447,088

(22) Filed: Apr. 13, 2012

(65) Prior Publication Data

US 2012/0266264 A1 Oct. 18, 2012

Related U.S. Application Data

(62) Division of application No. 12/875,884, filed on Sep. 3, 2010, now Pat. No. 8,163,283.

(60) Provisional application No. 61/239,704, filed on Sep. 3, 2009, provisional application No. 61/377,812, filed on Aug. 27, 2010.

(51) Int. Cl.
*C12N 5/00* (2006.01)
(52) U.S. Cl. .................. 435/328; 530/387.3; 435/320.1
(58) Field of Classification Search .................. None
See application file for complete search history.

(56) References Cited

U.S. PATENT DOCUMENTS 8,163,283 B2 * 4/2012 Lee ........................... 424/133.1

* cited by examiner

*Primary Examiner* — Sheela J Huff
(74) *Attorney, Agent, or Firm* — Morrison & Foerster LLP

(57) ABSTRACT

Monoclonal antibodies against gonadotropin releasing hormone (GnRH) receptor induce cellular apoptosis of various cancer cells expressing this surface receptor. The monoclonal antibodies and their humanized forms, or fragments thereof, can serve as anti-cancer agents for the treatment of cancer in humans, and can function as analogs of GnRH to affect regulation of reproductive functions or fertility in humans.

8 Claims, 8 Drawing Sheets

(A) Immunoglobulin light chains (κ) of GHR-106

```
                          LEADER
      ATGGATTCACAGGCCCAGGTTCTTATATTGCTGCTGCTATGGGTATCTGGTACCTGTGGG
       M  D  S  Q  A  Q  V  L  L  L  L  L  W  V  S  G  T  C  G

FR1
      GACATTGTGATGTCACAGTCTCCATCCTCCCTGGCTGTGTCAGCAGGAGAGAAGGTCACT
       D  I  V  M  S  Q  S  P  S  S  L  A  V  S  A  G  E  K  V  T

CDR1
      ATGAGCTGCAAATCCAGTCAGAGTGTGCTCAACAGTAGAACCCGAAAGAACTACTTGGCT
       M  S  C  K  S  S  Q  S  L  L  N  S  R  T  R  K  N  Y  L  A

FR2                              CDR2
      TGGTACCAGCAGAAACCAGGGCAGTCTCCTAAACTGCTGATCTACTGGGCATCCACTAGG
       W  Y  Q  Q  K  P  G  Q  S  P  K  L  L  I  Y  W  A  S  T  R

FR3
      GAATCTGGGGTCCCTGATCGCTTCACAGGCAGTGGATCTGGGACAGATTTCACTCTCACC
       E  S  G  V  P  D  R  F  T  G  S  G  S  G  T  D  F  T  L  T

CDR3
      ATCAGCAGTGTGCAGGCTGAAGACCTGGCAGTTTATTACTGCAAGCAATCTTATAATCTT
       I  S  S  V  Q  A  E  D  L  A  V  Y  Y  C  K  Q  S  Y  N  L

FR4
      TACACGTTCGGAGGGGGGACCAAGCTGGAAATAAAA
       Y  T  F  G  G  G  T  K  L  E  I  K
```

Figure 1A

(B) Immunoglobulin heavy chains of GHR-106

FR1
CAGGTGCAGCTGAAGGAGTCAGGACCTGGCCTGGTGGCACCCTCACAGAGCCTGTCCATC
Q  V  Q  L  K  E  S  G  P  G  L  V  A  P  S  Q  S  L  S  I

CDR1
ACATGCACTGTCTCTGGGTTCTCATTATCCAGATATAGTGTACACTGGGTTCGCCAGCCT
T  C  T  V  S  G  F  S  L  S  R  Y  S  V  H  W  V  R  Q  P

FR2                                    CDR2
CCAGGAAAGGGTCTGGAGTGGCTGGGAATGATATGGGGTGGTGGAAGCACAGACTATAAT
P  G  K  G  L  E  W  L  G  M  I  W  G  G  G  S  T  D  Y  N

FR3
TCAGCTCTCAAATCCAGACTGAGCATCAGCAAGGACAACTCCAAGAGCCAAGTTTTCTTA
S  A  L  K  S  R  L  S  I  S  K  D  N  S  K  S  Q  V  F  L

AAAATGAACAGTCTGCAAACTGATGACACAGCCATGTACTACTGTGCCAGAGGCAATGAT
K  M  N  S  L  Q  T  D  D  T  A  M  Y  Y  C  A  R  G  N  D

CDR3                    FR4
GGTTACTACTCGTTTGCTTACTGGGGCCAAGGGACTCTGGTCACTGTCTCTTCA
G  Y  Y  S  F  A  Y  W  G  Q  G  T  L  V  T  V  S  S

Figure 1B

Results of Immunohistochemical staining of GnRH receptor in different stages of ovarian cancer

SEQUENCE LISTING

```
<160> NUMBER OF SEQ ID NOS: 23

<210> SEQ ID NO 1
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: PEPTIDE
<222> LOCATION: (1)...(5)
<223> OTHER INFORMATION: sequence encoding CDR1 heavy chain region of
      GHR106

<400> SEQUENCE: 1

Arg Tyr Ser Val His
1               5

<210> SEQ ID NO 2
<211> LENGTH: 16
<212> TYPE: PRT
<213> ORGANISM: Artificial Sequence
<220> FEATURE:
<223> OTHER INFORMATION: Synthetic construct
<220> FEATURE:
<221> NAME/KEY: PEPTIDE
<222> LOCATION: (1)...(16)
<223> OTHER INFORMATION: sequence encoding CDR2 heavy chain region of
      GHR106

<400> SEQUENCE: 2

Met Ile Trp Gly Gly Gly Ser Thr Asp Tyr Asn Ser Ala Leu Lys Ser
1               5                   10                  15

<210> SEQ ID NO 3
<211> LENGTH: 10
<212> TYPE: PRT
<213> ORGANISM: Artificial Sequence
```

```
<220> FEATURE:
<223> OTHER INFORMATION: Synthetic construct
<220> FEATURE:
<221> NAME/KEY: PEPTIDE
<222> LOCATION: (1)...(10)
<223> OTHER INFORMATION: sequence encoding CDR3 heavy chain region of
      GHR106

<400> SEQUENCE: 3

Gly Asn Asp Gly Tyr Tyr Ser Phe Ala Tyr
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Synthetic construct
<220> FEATURE:
<221> NAME/KEY: PEPTIDE
<222> LOCATION: (1)...(17)
<223> OTHER INFORMATION: sequence encoding CDR1 light chain region of
      GHR106

<400> SEQUENCE: 4

Lys Ser Ser Gln Ser Leu Leu Asn Ser Arg Thr Arg Lys Asn Tyr Leu
1               5                   10                  15
Ala

<210> SEQ ID NO 5
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: PEPTIDE
<222> LOCATION: (1)...(7)
<223> OTHER INFORMATION: sequence encoding CDR2 light chain region of
      GHR106

<400> SEQUENCE: 5

Trp Ala Ser Thr Arg Glu Ser
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: PEPTIDE
<222> LOCATION: (1)...(8)
<223> OTHER INFORMATION: sequence encoding CDR3 light chain region of
      GHR106

<400> SEQUENCE: 6

Lys Gln Ser Tyr Asn Leu Tyr Thr
1               5

<210> SEQ ID NO 7
<211> LENGTH: 29
<212> TYPE: PRT
<213> ORGANISM: Homo sapiens
<220> FEATURE:
<221> NAME/KEY: PEPTIDE
<222> LOCATION: (1)...(29)
<223> OTHER INFORMATION: extracellular domain of human GnRH receptor

<400> SEQUENCE: 7
```

```
Met Ala Asn Ser Ala Ser Pro Glu Gln Asn Gln Asn His Cys Ser Ala
 1               5                  10                  15

Ile Asn Asn Ser Ile Pro Leu Met Gln Gly Asn Leu Pro
             20                  25
```

<210> SEQ ID NO 8
<211> LENGTH: 132
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(132)
<223> OTHER INFORMATION: light chain amino acid sequence encoded by
      monoclonal antibody GHR106

<400> SEQUENCE: 8

```
Met Asp Ser Gln Ala Gln Val Leu Ile Leu Leu Leu Leu Trp Val Ser
 1               5                  10                  15

Gly Thr Cys Gly Asp Ile Val Met Ser Gln Ser Pro Ser Ser Leu Ala
             20                  25                  30

Val Ser Ala Gly Glu Lys Val Thr Met Ser Cys Lys Ser Ser Gln Ser
         35                  40                  45

Leu Leu Asn Ser Arg Thr Arg Lys Asn Tyr Leu Ala Trp Tyr Gln Gln
     50                  55                  60

Lys Pro Gly Gln Ser Pro Lys Leu Leu Ile Tyr Trp Ala Ser Thr Arg
 65                  70                  75                  80

Glu Ser Gly Val Pro Asp Arg Phe Thr Gly Ser Gly Ser Gly Thr Asp
                 85                  90                  95

Phe Thr Leu Thr Ile Ser Ser Val Gln Ala Glu Asp Leu Ala Val Tyr
            100                 105                 110

Tyr Cys Lys Gln Ser Tyr Asn Leu Tyr Thr Phe Gly Gly Gly Thr Lys
        115                 120                 125

Leu Glu Ile Lys
    130
```

<210> SEQ ID NO 9
<211> LENGTH: 118
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(118)
<223> OTHER INFORMATION: heavy chain sequence encoded by monoclonal
      antibody GHR106

<400> SEQUENCE: 9

```
Gln Val Gln Leu Lys Glu Ser Gly Pro Gly Leu Val Ala Pro Ser Gln
 1               5                  10                  15

Ser Leu Ser Ile Thr Cys Thr Val Ser Gly Phe Ser Leu Ser Arg Tyr
             20                  25                  30

Ser Val His Trp Val Arg Gln Pro Pro Gly Lys Gly Leu Glu Trp Leu
         35                  40                  45

Gly Met Ile Trp Gly Gly Gly Ser Thr Asp Tyr Asn Ser Ala Leu Lys
     50                  55                  60

Ser Arg Leu Ser Ile Ser Lys Asp Asn Ser Lys Ser Gln Val Phe Leu
 65                  70                  75                  80

Lys Met Asn Ser Leu Gln Thr Asp Asp Thr Ala Met Tyr Tyr Cys Ala
```

```
                    85                  90                  95
Arg Gly Asn Asp Gly Tyr Tyr Ser Phe Ala Tyr Trp Gly Gln Gly Thr
               100                 105                 110

Leu Val Thr Val Ser Ser
        115

<210> SEQ ID NO 10
<211> LENGTH: 25
<212> TYPE: DNA
<213> ORGANISM: Artificial Sequence
<220> FEATURE:
<223> OTHER INFORMATION: synthetically constructed sense primer GnRHR1

<400> SEQUENCE: 10
cagaagaaag agaaagggaa aaagc                                          25

<210> SEQ ID NO 11
<211> LENGTH: 25
<212> TYPE: DNA
<213> ORGANISM: Artificial Sequence
<220> FEATURE:
<223> OTHER INFORMATION: Synthetically constructed antisense primer
      GnRHR1

<400> SEQUENCE: 11
gatgaaaaga gggatgatga agagg                                          25

<210> SEQ ID NO 12
<211> LENGTH: 25
<212> TYPE: DNA
<213> ORGANISM: Artificial Sequence
<220> FEATURE:
<223> OTHER INFORMATION: Synthetically constructed sense amplification
      primer

<400> SEQUENCE: 12
gatgaaaaga gggatgatga agagg                                          25

<210> SEQ ID NO 13
<211> LENGTH: 19
<212> TYPE: DNA
<213> ORGANISM: Artificial Sequence
<220> FEATURE:
<223> OTHER INFORMATION: Synthetically constructed antisense
      amplification primer

<400> SEQUENCE: 13
gtagccaatc tgcagacag                                                 19

<210> SEQ ID NO 14
<211> LENGTH: 18
<212> TYPE: DNA
<213> ORGANISM: Artificial Sequence
<220> FEATURE:
<223> OTHER INFORMATION: Synthetically constructed sense amplification
      primer

<400> SEQUENCE: 14
caaggtgctc ggtccttc                                                  18

<210> SEQ ID NO 15
<211> LENGTH: 19
<212> TYPE: DNA
<213> ORGANISM: Artificial Sequence
<220> FEATURE:
<223> OTHER INFORMATION: Synthetically constructed antisense
      amplification primer
```

```
<400> SEQUENCE: 15
gaacatgtta taaaagagg                                                    19

<210> SEQ ID NO 16
<211> LENGTH: 17
<212> TYPE: DNA
<213> ORGANISM: Artificial Sequence
<220> FEATURE:
<223> OTHER INFORMATION: Synthetically constructed sense amplification
      primer

<400> SEQUENCE: 16
tccgccgcag acgccgc                                                      17

<210> SEQ ID NO 17
<211> LENGTH: 18
<212> TYPE: DNA
<213> ORGANISM: Artificial Sequence
<220> FEATURE:
<223> OTHER INFORMATION: Synthetically constructed antisense
      amplification primer

<400> SEQUENCE: 17
tgcaggggag caggaatt                                                     18

<210> SEQ ID NO 18
<211> LENGTH: 20
<212> TYPE: DNA
<213> ORGANISM: Artificial Sequence
<220> FEATURE:
<223> OTHER INFORMATION: Synthetically constructed sense amplification
      primer

<400> SEQUENCE: 18
cagaagcgag atgacgaagg                                                   20

<210> SEQ ID NO 19
<211> LENGTH: 21
<212> TYPE: DNA
<213> ORGANISM: Artificial Sequence
<220> FEATURE:
<223> OTHER INFORMATION: Synthetically constructed antisense
      amplification primer

<400> SEQUENCE: 19
ccagaacatt tattgcatga c                                                 21

<210> SEQ ID NO 20
<211> LENGTH: 21
<212> TYPE: DNA
<213> ORGANISM: Artificial Sequence
<220> FEATURE:
<223> OTHER INFORMATION: Synthetically constructed sense amplification
      primer

<400> SEQUENCE: 20
gaaatcccat caccatcttc c                                                 21

<210> SEQ ID NO 21
<211> LENGTH: 20
<212> TYPE: DNA
<213> ORGANISM: Artificial Sequence
<220> FEATURE:
<223> OTHER INFORMATION: Synthetically constructed antisense
      amplification primer

<400> SEQUENCE: 21
```
ccaggggtct tactccttgg                                                   20

<210> SEQ ID NO 22
<211> LENGTH: 396
<212> TYPE: DNA
<213> ORGANISM: Artificial Sequence
<220> FEATURE:
<223> OTHER INFORMATION: Synthetically constructed monoclonal antibody
      GHR106
<220> FEATURE:
<221> NAME/KEY: CDS
<222> LOCATION: (1)...(396)

<400> SEQUENCE: 22

```
atg gat tca cag gcc cag gtt ctt ata ttg ctg cta tgg gta tct         48
Met Asp Ser Gln Ala Gln Val Leu Ile Leu Leu Leu Trp Val Ser
1               5                   10                  15 ggt acc tgt ggg gac att gtg atg tca cag tct cca tcc tcc ctg gct     96
Gly Thr Cys Gly Asp Ile Val Met Ser Gln Ser Pro Ser Ser Leu Ala
                20                  25                  30 gtg tca gca gga gag aag gtc act atg agc tgc aaa tcc agt cag agt    144
Val Ser Ala Gly Glu Lys Val Thr Met Ser Cys Lys Ser Ser Gln Ser
        35                  40                  45 ctg ctc aac agt aga acc cga aag aac tac ttg gct tgg tac cag cag    192
Leu Leu Asn Ser Arg Thr Arg Lys Asn Tyr Leu Ala Trp Tyr Gln Gln
    50                  55                  60 aaa cca ggg cag tct cct aaa ctg ctg atc tac tgg gca tcc act agg    240
Lys Pro Gly Gln Ser Pro Lys Leu Leu Ile Tyr Trp Ala Ser Thr Arg
65              70                  75                  80 gaa tct ggg gtc cct gat cgc ttc aca ggc agt gga tct ggg aca gat    288
Glu Ser Gly Val Pro Asp Arg Phe Thr Gly Ser Gly Ser Gly Thr Asp
                85                  90                  95 ttc act ctc acc atc agc agt gtg cag gct gaa gac ctg gca gtt tat    336
Phe Thr Leu Thr Ile Ser Ser Val Gln Ala Glu Asp Leu Ala Val Tyr
            100                 105                 110 tac tgc aag caa tct tat aat ctt tac acg ttc gga ggg ggg acc aag    384
Tyr Cys Lys Gln Ser Tyr Asn Leu Tyr Thr Phe Gly Gly Gly Thr Lys
        115                 120                 125 ctg gaa ata aaa                                                    396
Leu Glu Ile Lys
    130
```

<210> SEQ ID NO 23
<211> LENGTH: 354
<212> TYPE: DNA
<213> ORGANISM: Artificial Sequence
<220> FEATURE:
<223> OTHER INFORMATION: Synthetically constructed monoclonal antibody
      GHR106
<220> FEATURE:
<221> NAME/KEY: CDS
<222> LOCATION: (1)...(354)

<400> SEQUENCE: 23

```
cag gtg cag ctg aag gag tca gga cct ggc ctg gtg gca ccc tca cag     48
Gln Val Gln Leu Lys Glu Ser Gly Pro Gly Leu Val Ala Pro Ser Gln
1               5                   10                  15 agc ctg tcc atc aca tgc act gtc tct ggg ttc tca tta tcc aga tat     96
Ser Leu Ser Ile Thr Cys Thr Val Ser Gly Phe Ser Leu Ser Arg Tyr
                20                  25                  30 agt gta cac tgg gtt cgc cag cct cca gga aag ggt ctg gag tgg ctg    144
Ser Val His Trp Val Arg Gln Pro Pro Gly Lys Gly Leu Glu Trp Leu
        35                  40                  45 gga atg ata tgg ggt ggt gga agc aca gac tat aat tca gct ctc aaa    192
```

| | | | | | | | | | | | | | | |
|---|---|---|---|---|---|---|---|---|---|---|---|---|---|---|
| Gly | Met | Ile | Trp | Gly | Gly | Ser | Thr | Asp | Tyr | Asn | Ser | Ala | Leu | Lys |
| | 50 | | | | 55 | | | | 60 | | | | | |
| tcc | aga | ctg | agc | atc | agc | aag | gac | aac | tcc | aag | agc | caa | gtt | ttc | tta | 240
| Ser | Arg | Leu | Ser | Ile | Ser | Lys | Asp | Asn | Ser | Lys | Ser | Gln | Val | Phe | Leu |
| 65 | | | | | 70 | | | | | 75 | | | | | 80 |
| aaa | atg | aac | agt | ctg | caa | act | gat | gac | aca | gcc | atg | tac | tac | tgt | gcc | 288
| Lys | Met | Asn | Ser | Leu | Gln | Thr | Asp | Asp | Thr | Ala | Met | Tyr | Tyr | Cys | Ala |
| | | | | 85 | | | | | 90 | | | | | 95 | |
| aga | ggc | aat | gat | ggt | tac | tac | tcg | ttt | gct | tac | tgg | ggc | caa | ggg | act | 336
| Arg | Gly | Asn | Asp | Gly | Tyr | Tyr | Ser | Phe | Ala | Tyr | Trp | Gly | Gln | Gly | Thr |
| | | | 100 | | | | | 105 | | | | | 110 | | |
| ctg | gtc | act | gtc | tct | tca | | | | | | | | | | | 354
| Leu | Val | Thr | Val | Ser | Ser | | | | | | | | | | |
| | | 115 | | | | | | | | | | | | | |

MONOCLONAL ANTIBODIES AGAINST GONADOTROPIN-RELEASING HORMONE RECEPTOR

CROSS-REFERENCE TO RELATED APPLICATIONS

This application is a divisional of U.S. application Ser. No. 12/875,884 filed 3 Sep. 2010, now U.S. Pat. No. 8,163,283, which claims priority from U.S. provisional application 61/239,704 filed 3 Sep. 2009 and U.S. provisional application 61/377,812 filed 27 Aug. 2010. The disclosures of which are herein incorporated by reference in their entirety.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 616342000210Seqlist.txt | May 31, 2012 | 11,435 bytes |

TECHNICAL FIELD

The invention is in the field of cancer treatment and diagnosis. More specifically, the invention concerns monoclonal antibodies immunoreactive with the gonadotropin releasing hormone (GnRH) receptor, in particular with the extracellular domains of the GnRH receptor.

BACKGROUND ART

Gonadotropin releasing hormone (GnRH), both types I and II, is a decapeptide hormone that stimulates the release of gonadotropin, luteinizing hormone (LH) and follicle stimulating hormone (FSH) from the anterior pituitary through specific binding to the GnRH receptor (GnRHR) located on the external membrane of selected cell types. Subsequent studies revealed that GnRH and its receptor also play extra-pituitary roles in numerous normal and malignant cells or tissues, the mechanisms of which are still being actively explored. Lee, G-C. Y., et al., *Am J Reprod Immunol* (2000) 44:170-177, Chien, C. H., et al., *Int J Gynecol Cancer* (2004) 14:451-458. Anti-proliferative effects of GnRH or its analogs on cancer cells of different human tissue origins have been reported. (Pati, D., et al., *Endocrin* (1995) 136:75-84; Choi, K. C., et al., *J Clin Endocrinol & Metab* (2001) 86:5075-5078).

Numerous clinical studies have also reported the use of cytotoxic GnRH analogs or GnRH analogs alone as anti-cancer drugs. To improve efficacy, GnRH analogs are sometimes formulated by covalently linking cytotoxic anti-cancer agents, such as AN-152 or AN-207, to GnRH or its analogs. GnRH agonists or antagonists have been reported to suppress cancer cell growth clinically. GnRH analogs, such as Leuprorelin, Buserelin and Goserelin, have been used in the treatment of hormone-responsive cancers, such as prostate and breast cancers. (Gnananpragasam, V. J., et al., *J Pathol* (2005) 206:205-213; So, W. K., et al., *FEBS Journal* (2008) 275: 5496-5511.) However, limited and variable efficacy was observed in many cases. Nevertheless, this approach has been shown to be effective in cancer treatments with lower toxicity and improved efficacy when compared to non-targeted systemic chemotherapy. (Nagy, A., et al., *Biol of Reprod* (2005) 73:851-859).

GnRH analogs have also been used for the treatment of other estrogen-dependent conditions, such as endometriosis, uterine fibroids, and endometrial thinning, to treat precocious puberty, and to control ovarian stimulation in In Vitro Fertilization (IVF).

While it has been established that GnRH and its analogs exhibit antiproliferative effects on cancer cells or tissues, the efficacy of GnRH and its analogs is limited by the relatively short half life in circulation. For example, GnRH has a half life of only 2-4 minutes, while decapeptide GnRH analogs have half-lives of a few hours. Therefore, the use of GnRH or its analogs as drugs generally requires frequent administration. There remains a need for the development of alternate approaches for the treatment of these conditions, using agents having improved half-lives, efficacy and/or tolerability.

The development of antibody-based anti-cancer drugs as an alternative to traditional agents in human cancer treatments has been explored in recent years. It is important that the drug target on the cancer cell surface be clearly identified, expressed with high abundance and its mechanisms of action be well elucidated.

Monoclonal antibodies generally have a relatively long half life in human circulation, typically ranging from about 5 days to 22 days. Thus, the use of monoclonal antibodies as drugs provides an attractive alternative for the treatment of cancer, and antibodies targeting the GnRH receptor provides a major advantage over the decapeptide GnRH analogs due to the much longer half life in circulation (e.g., from 5 days to 22 days versus hours for the peptidic GnRH analogs). In particular, monoclonal antibodies to the GnRH receptor may be useful for the treatment of hormone sensitive cancers, such as prostate and breast cancers, and for the regulation of fertility. Such antibodies may also have a reduced potential for side effects.

A monoclonal antibody against a synthetic peptide corresponding to amino acids 1-29 of the N-terminal extracellular domain of the human GnRH receptor has been reported to bind to a human breast carcinoma and an ovarian carcinoma cell line. Karande, A., et al., *Mol. Cell. Endocrin.* (1995) 114:51-56; Rajeshwari, K. & Karande, A., *Immunol. Invest.* (1999) 28:103-14. A monoclonal antibody against a synthetic peptide corresponding to amino acids 5-17 of the N-terminal extracellular domain of the mouse hypophyseal GnRH receptor has been reported to react with a human ovarian cancer cell line and to inhibit endometrial maturation in mice. Ackerman, R. C., et al., *Cancer Lett.* (1994) 81:177-84; Asirvatham, A. L., et al., *Am. J. Reprod. Immunol.* (1994) 32:95-100.

The generation of anti-GnRH receptor antibodies for the diagnosis and treatment of reproductive disorders and for contraception is disclosed in U.S. Pat. No. 5,750,366. The generation of antibodies to the type II receptor for contraception is also disclosed in US 2003/0124585, as is the use of such antibodies in the treatment of cancer. US 2006/0193853 may suggest the use of anti-GnRH receptor antibodies among many other entities in combination with a growth regulating factor for the treatment of cancer. US 2005/0158309 discloses anti-GnRH receptor antibodies among many other candidates for the treatment of T-cell related neoplastic diseases. US 2003/144203 suggests, among many other candidates, raising antibodies to GnRHR to delay senescence. US 2006/0148697 discloses (again, among many other alternatives) the use of a vaccine or antibody to stimulate the production of antibodies that block the GnRH-receptor as potentially useful for the treatment of brain cancer. None of these documents discloses the preparation of monoclonal antibodies or isolated antibody preparation useful in such treatments.

DISCLOSURE OF THE INVENTION

The present invention provides monoclonal antibodies that react specifically with the human GnRH-receptor and demonstrate biological effects on cancer cells similar to those provided by GnRH and its peptide analogs (agonists and antagonists), but offer important advantages of extended half life, thus permitting administration only once every several weeks, as opposed to administration three times daily (e.g., Buserelin) or every other day. Monoclonal antibodies to the GnRH receptor can also alter reproductive functions, and are useful for the treatment of conditions similar to those treated with GnRH analogs, offering similar advantages associated with long half life.

One embodiment of the present invention provides a monoclonal antibody designated as GHR-106 which demonstrates high affinity and specificity to the human GnRH receptor, comparable to that of GnRH or its analogs and has a long half life in circulation.

The GHR-106 monoclonal antibody has been shown to induce apoptosis in cancer cell cultures in vitro similar to that observed by GnRH or its peptide analogs. Therefore, GHR-106 with a long circulation half life can function as one of the GnRH peptide analogs but with certain long acting properties. This unique property of long circulation half life could be more beneficial in cancer treatment than GnRH or its decapeptide analogs. Therefore, frequent administration with antibody drugs can be avoided and the efficacy of the drug treatment may also be enhanced accordingly.

As demonstrated below, the GnRH receptor is selectively expressed on tumor cells compared to corresponding normal tissue and the level of expression correlates with the severity of the tumor, and monoclonal antibodies specific for this receptor have been prepared. These antibodies offer a unique approach to cancer treatment and detection.

Thus, in one aspect, the invention is directed to monoclonal antibodies or fragments thereof that selectively bind the extracellular domain of human GnRH receptor. In some embodiments, the monoclonal antibodies or immunoreactive fragments bind to an epitope within approximately positions 1-29 of the N-terminus of the GnRH receptor, bind with high affinity, and compete with GnRH for the receptor. The antibodies include humanized forms. These antibodies affect apoptosis of targeted cells. Without wishing to be bound by theory, the induction of apoptosis is believed to occur by down-regulation of certain ribosomal proteins. (Chen, A., et al., Cancer Res. (2002) 1036-1044).

The antibodies of the invention may be produced recombinantly or secreted by immortalized or hybridoma cells. They may also be produced using transgenic plants or animals. Thus, in additional aspects, the invention relates to these means for production and the cells and organisms useful in these methods.

In another aspect, the invention provides a method to inhibit cell proliferation, comprising administering the antibodies of the invention to a cell or tissue, which may be contained in a subject.

In another aspect, the invention provides a method for treating a proliferative disorder, comprising administering to a subject in need thereof an effective amount of an antibody of the invention or pharmaceutical composition thereof. The proliferative disorder can be cancer, or it can be a benign proliferative condition.

In a further aspect, the invention provides a method for controlling ovarian stimulation in assisted reproduction methods, such as IVF, comprising administering to a subject in need thereof an effective amount of an antibody or fragment of the invention, or a humanized form or pharmaceutical composition thereof.

In another aspect, the invention provides a method for detecting neoplastic cells, comprising contacting a biological sample with the antibody of the invention and detecting any binding to the sample, wherein said binding to the sample indicates the presence of GnRH receptors on cells in the sample, indicating said cells are neoplastic.

BRIEF DESCRIPTION OF THE DRAWINGS

FIGS. 1A and 1B show the encoding nucleotide sequences (SEQ ID NOS:22-23) and deduced amino acid sequences (SEQ ID NOS:8-9) of heavy and light chain variable regions of GHR-106. The amino acid sequence of GHR-103 was determined to be the same as that of GHR-106.

MODES OF CARRYING OUT THE INVENTION

Figure 2:
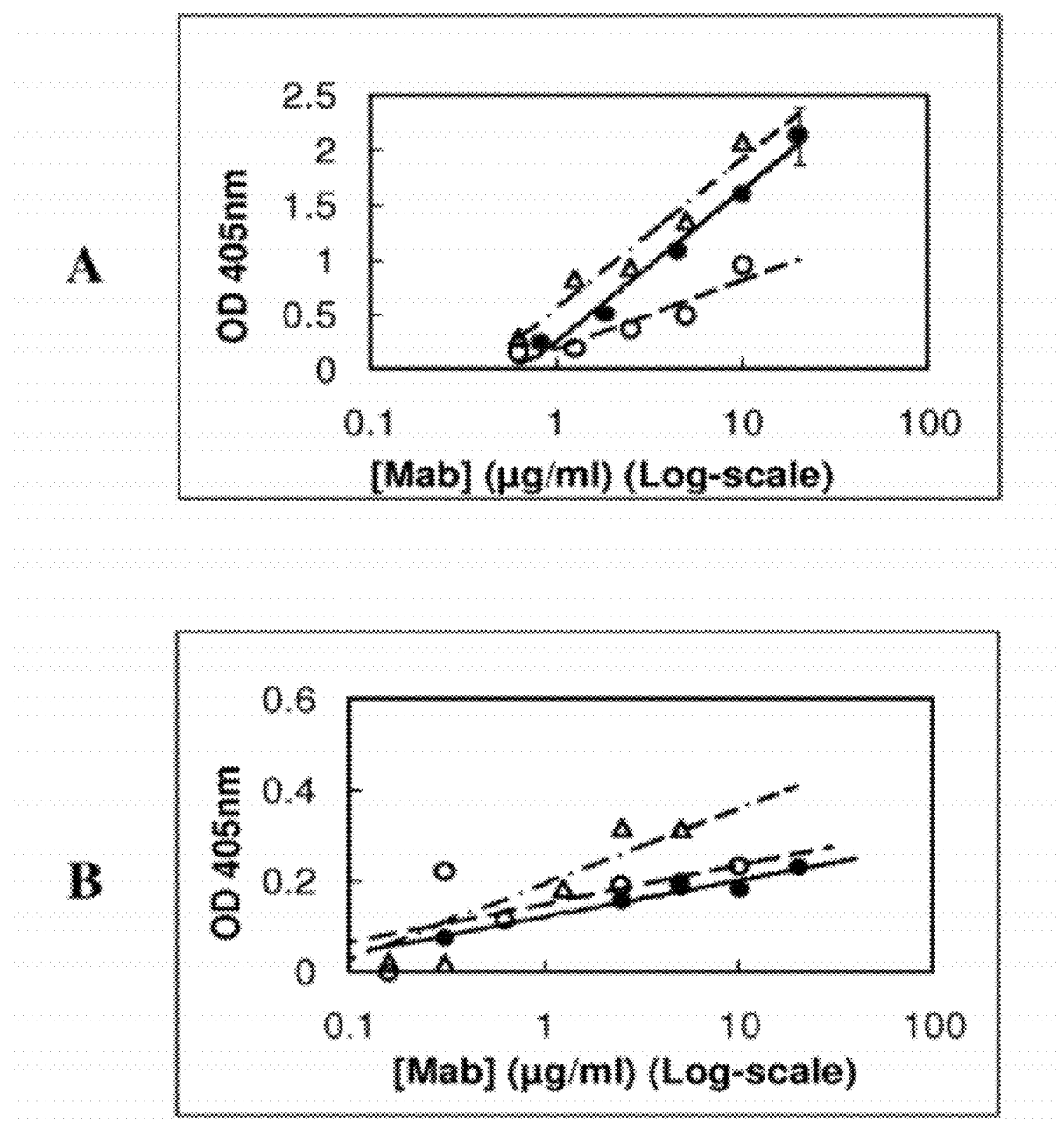
FIGS. 2A and 2B show the results of an ELISA to determine dose-dependent binding of GHR-103, 106, 114 monoclonal antibodies to well-coated synthetic peptide corresponding to the N-terminal 1-29 amino acid residues of human GnRH receptor and OC-3-VGH cancer cells, respectively. (Δ: GHR-103; ●: GHR-106; ○: GHR-114).

The present invention includes monoclonal antibodies that bind to the extracellular domains of the human GnRH receptor, in particular antibodies that bind to N-terminal amino acid positions 1-29, have an affinity for GnRH receptor of at least that associated with a dissociation constant ($K_D$) of $10^{-7}$M or $10^{-8}$M, and compete with GnRH for binding to the receptor.

The term "antibodies" refers not only to complete forms of the antibodies, but also to immunoreactive fragments thereof. The immunoreactive fragments include the variable regions of the antibody chains and may be obtained by proteolytic cleavage of the complete antibody, or may be produced recombinantly, including in single-chain forms. Human forms of the antibodies are preferred for use in treatment of humans, and such human forms may be obtained by humanizing antibodies produced in other organisms such as mice or mammalian cell cultures, by using well known techniques. Alternatively, human forms may be produced in transgenic animals, such as the XenoMouse®, or isolated from human cells.

As is understood in the art, the immunospecificity of antibodies is determined by the CDR regions thereof, and thus, the invention includes antibodies with specified sequences characterizing the CDR portions of the heavy and light chains.

Thus, in some embodiments, the invention includes antibodies or fragments wherein the CDR1 region of the heavy chain is encoded by a peptide of sequence RYSVH (SEQ ID NO:1) or a sequence having at least 90% sequence identity to SEQ ID NO:1; the CDR2 region of the heavy chain is encoded by the peptide sequence MIWGGGSTDYNSALKS (SEQ ID NO:2) or a sequence having at least 90% sequence identity to SEQ ID NO:2; the CDR3 region of the heavy chain is encoded by the peptide of sequence GNDGYYSFAY (SEQ ID NO:3) or a sequence having at least 90% sequence identity to SEQ ID NO:3; the CDR1 region of the light chain is encoded by the peptide sequence KSSQSLLNSRTRKNYLA (SEQ ID NO:4) or a sequence having at least 90% sequence identity to SEQ ID NO:4; the CDR2 region of the light chain is encoded by the peptide sequence WASTRES (SEQ ID NO:5) or a sequence having at least 90% sequence identity to SEQ ID NO:5; or the CDR3 region of light chain is encoded by the peptide sequence KQSYNLYT (SEQ ID NO:6) or a sequence having at least 90% sequence identity to SEQ ID NO:6, or combinations thereof.

In some embodiments, the invention includes antibodies or fragments wherein the peptide encoding the CDR1 region of the heavy chain is SEQ ID NO:1; the peptide encoding the CDR2 region of the heavy chain is SEQ ID NO:2; the peptide encoding the CDR3 region of the heavy chain is SEQ ID NO:3; the peptide encoding the CDR1 region of the light chain is SEQ ID NO:4; the peptide encoding the CDR2 region of the light chain is SEQ ID NO:5; or the peptide encoding the CDR3 region of the light chain is SEQ ID NO:6, or combinations thereof.

In other embodiments, the invention provides antibodies or fragments having a combination of two or more of these sequences in the CDR regions.

The invention also provides sequences of the variable regions having at least 80%, 90%, 95%, 96%, 97%, 98%, 99%, or greater than 99% sequence identity to these sequences.

The invention also provides antibodies or fragments comprising the variable regions of GHR-106.

The invention further provides an antibody having a light chain sequence having at least 80%, 90%, 95%, 96%, 97%, 98%, 99%, or greater than 99% sequence identity to the sequence: MDSQAQVLILLLLWVSGTCGDIVM-SQSPSSLAVSAGEKVTMSCKSSQSLLNS RTRKNY-LAWYQQKPGQSPKLLIYWASTRESGVP-DRFTGSGSGTDFTLTISSVQAEDLAV YYCKQSYNLYTFGGGTKLEIK (SEQ ID NO:8) and/or having a heavy chain sequence having at least 80%, 90%, 95%, 96%, 97%, 98%, 99%, or greater than 99% sequence identity to the sequence: QVQLKESG-PGLVAPSQSLSITCTVSGFSLSRYSVH-WVRQPPGKGLEWLGM IWGGGSTDYNSALKSRL-SISKDNSKSQVFLKMNSLQTDDTAMYYCARG NDGYYSFAY WGQGTLVTVSS (SEQ ID NO:9).

Immunogenic peptides of positions 1-29 of the GnRH N-terminal extracellular portion, having the sequence MAN-SASPEQNQNHCSAINNSIPLMQGNLP (SEQ ID NO:7), may be used as immunogens when coupled, if needed, to an immunogenicity enhancing portion, such as a toxoid or KLH. Typical subjects for immunization include laboratory animals such as mice, rats or rabbits as well as larger animals such as sheep or goats. For preparation of monoclonal antibodies, laboratory animals are typically used since spleens are harvested to obtain the pertinent antibody-producing cells. However, using currently available techniques, antibody producing cells of appropriate specificity may also be isolated from the peripheral blood. As noted above, the framework regions may be modified to humanize any antibodies derived from non-human sources.

The antibodies of the invention bind to the GnRH receptor in the extracellular region and typically with significant affinity. The antibodies of the invention will have affinities associated with a dissociation constant ($K_D$) of $10^{-7}$ M or less, e.g., $10^{-8}$, $10^{-9}$ M, or $10^{-10}$ M, or values intermediate between these. Preferably, the dissociation constant is about $10^{-8}$M or less.

The monoclonal antibodies of the invention or their immunoreactive fragments may be prepared by a variety of techniques, including recombinant production. Thus, encoding sequences isolated from cells secreting the antibodies are obtained and included in expression systems operable in a variety of hosts, including microbial hosts, mammalian cells, plant cells, and insect cells. Transgenic animals and plants also may be used to produce these antibodies or immunoreactive fragments. The availability of the encoding nucleotide sequences also provides the opportunity for humanization using techniques well known in the art.

The antibodies of the invention bind to a variety of cancer cells or rapidly proliferating cells in general and are useful in mitigating the proliferation thereof. Therefore, they are useful in treating hyperproliferative diseases such as cancer or benign hypertrophies. The antibodies or fragments may also be coupled to therapeutic agents, including toxins to enhance their effect in inhibiting proliferation.

The antibodies of the invention induce apoptosis in cultured cancer cells in vitro and in vivo and have a relatively long half life in circulation when compared to GnRH or its analogs. Therefore, humanized forms of these monoclonal antibodies may offer advantages over the use of GnRH hormone or GnRH analogs in treating a variety of human cancers. Cytotoxic mechanisms, such as CDC (complement-dependent cytotoxicity) or ADCC (antibody-dependent cellular cytotoxicity) cannot be ruled out upon contact (binding) between a humanized monoclonal antibody such as a humanized form of GHR-106 (e.g., IgG or $IgG_4$ isoform), and the GnRH receptor on the cancer cell surface.

In certain embodiments, the antibodies of the present invention may be used for the treatment of cancers, including cancer of the prostate, breast, ovary, endometrium, cervix, pancreas, colon, lung, liver or kidney, among others. In addition, the type I GnRH receptor (GnRHR1) has been found to be overexpressed in cell lines derived from glioblastoma, lymphoma, leukemia, melanoma and neuroblastoma, and in some embodiments, the antibodies of the invention may also used for the treatment of these cancers.

Without wishing to be bound by theory, the antibodies of the present invention may act similarly to GnRH analogs to slow the growth of prostate cancer in men by blocking or otherwise inhibiting the production of androgens produced by the testes. In addition, these antibodies may reduce the ovarian secretion of estradiol and progesterone in women, leading to inhibition of estrogen-dependent cancers.

The antibodies of the present invention can also act similarly to GnRH analogs in hormonal actions, and are useful to effect fertility regulation or otherwise modulate human reproductive functions. In particular, the antibodies of the invention are useful for the treatment of disorders associated with abnormal expression of the GnRH-R; e.g., overexpression, underexpression or expression of a dysfunctional mutant receptor.

These antibodies are useful for the treatment of estrogen-dependent conditions, such as endometriosis, uterine fibroids, and endometrial thinning, to treat polycystic ovary disease, to treat precocious puberty. Additional benign proliferative disorders that can be treated with the antibodies provided herein include benign tumors such as endometrial hyperplasia, uterine leiomyoma, adenomyosis, and endometriosis.

The antibodies provided by the present invention are also useful to control ovarian stimulation in assisted reproduction methods, such as In vitro Fertilization (IVF) or egg donation. GnRH analogs (both agonists and antagonists) have been used in assisted reproduction to control ovulation, but require prolonged administration over a period of about 2 weeks, frequently by repeated (e.g., daily) subcutaneous injections or by an implanted device. Repeated treatment with GnRH agonists is believed to stimulate the over-production and depletion of LH and FSH. GnRH antagonists are believed to block the action of GnRH on the pituitary, suppressing the production of LH and FSH. The monoclonal antibodies of the present invention are useful to control ovarian stimulation in assisted reproduction methods, and have advantages over GnRH analogs due to their improved half life in circulation, which allows a reduction in the frequency of administration. This may reduce the incidence of side effects and lead to improved tolerability and patient compliance.

Pharmaceutical compositions comprising the invention antibodies and a pharmaceutically acceptable excipient are included in the invention. The pharmaceutical compositions are useful for prophylaxis or treatment including amelioration of cell proliferative disorders, such as cancer or inflammatory disorders, and may include additional therapeutic agents.

For use in therapy, antibodies or fragments of the invention are formulated into such pharmaceutical compositions using suitable excipients and administered according to standard protocols. The pharmaceutical compositions may have as their sole active ingredient the antibodies or fragments of the invention or additional therapeutic agents may be present, including other antibodies or fragments that are immunoreactive with the GnRH receptor, GnRH I or GnRH II, or analogs thereof, or other agents, such as chemotherapeutic agents that may be useful to treat the cell proliferative disorders. In addition, the compositions may include nutritional substances, such as vitamins, or other beneficial compounds or palliative agents other than an antibody.

Typically, antibodies are administered at dosage levels of 0.01-20 mg/kg of human subject or in amounts in the range of 0.01-5 mg/kg or intermediate amounts between these ranges. However, the dosage may be more or less than the ranges indicated, and the determination of an appropriate dosage or dosage range is within the skill of the ordinary practitioner. Repeated administration separated by several days or several weeks or several months may be beneficial. Administration of mixtures of immunogenic fragments or entire antibodies is also included within the scope of the invention.

Administration of the antibody compositions of the present invention is typically by injection, generally intravenous injection. Thus, parenteral administration is preferred. However, any workable mode of administration is included.

The formulations are prepared in ways generally known in the art for administering antibody compositions. Suitable formulations may be found in standard formularies, such as *Remington's Pharmaceutical Sciences*, latest edition, Mack Publishing Co., Easton, Pa., incorporated herein by reference. The formulations are typically those suitable for parenteral administration, including isotonic solutions, which include buffers, antioxidants and the like, as well as emulsions that include delivery vehicles such as liposomes, micelles and nanoparticles.

The desired protocols and formulations are dependent on the judgment of the attending practitioner as well as the specific condition of the subject. Accordingly, dosage levels will depend on the age, general health and the severity of the condition to be treated, if appropriate.

Since the GnRH receptor is produced at high levels on proliferating cells, the antibodies of the invention are also useful in detecting hyperproliferating cells in biological samples. Techniques for such immunoassays are well-established in the art. It may be desirable to label the antibodies with a detectable agent such as a radioactive material (e.g., radionuclide), an enzyme, a fluorescent label, or a cytotoxic drug label.

The following examples are offered to illustrate but not to limit the invention.

General Methods

Chemicals

All chemicals were purchased from Sigma Chemical company (St. Louis, Mo.) unless otherwise mentioned Cell Lines The ovarian cancer cell line, OC-3-VGH was established by Department of Obstetrics and Gynecology at Veterans General Hospital, Taipei, Taiwan and was cultured in RPMI medium containing 10% fetal calf serum. Human cancer cell lines were obtained from American Type Culture Collection (ATCC) Co. (Rockville, Md.) and were cultured and harvested separately according to the supplier's instructions.

Preparation A

Determination of GnRH Receptor in Cancer Cell Lines

Cancer cell lines were assessed to determine whether they expressed the gene for GnRH receptor as follows:

Total RNA was extracted from $10^5$-$10^7$ cells of each cell line using QIAGEN RNeasy mini kit. RNase-free DNase set was included to avoid genomic gene interference. Reverse transcription (RT) of total RNA (0.5 μg-5 μg/20 μl) to cDNA was performed by using oligo $(dT)_{15}$ primers and Easy-Script™ First Strand cDNA Synthesis Kit from Applied Biological Materials (Abm) Inc. (Richmond, BC, Canada) following the manufacturer's protocol. Reaction mixtures with RNA template but without reverse-transcriptase or with reverse-transcriptase but without RNA template were used as the negative controls for cDNA synthesis.

The resulting cDNA was amplified using the primers GnRHR1 (486 bp):

```
                                  (SEQ ID NO: 10)
5'-CAGAAGAAAGAGAAAGGGAAAAAGC-3' (sense)

and (SEQ ID NO: 11)
5'-GATGAAAAGAGGGATGATGAAGAGG-3' (antisense)

obtained from Integrated DNA Technologies (San
Diego, CA).
```

PCR was performed by using 2×PCR Plus MasterMix kit (ABM, Richmond, BC, Canada) according to manufacturer's protocols. After denaturing at 94° C. for 4 min, 20-35 cycles were performed under the following conditions: denaturing at 94° C. for 40 s; annealing at 50° C. for 40 s and polymerizing at 72° C. for 1 min and at last complete extension at 72° C. for 7 min. At the end, the PCR product was checked by 1.5% agarose gel electrophoresis. The relative signal intensities of different PCR products on the agarose gel were semi-quantitatively analyzed by using ImageQuant image analysis software. The intensity of GAPDH control was adjusted to 100% in each case for comparative purposes. The negative control from cDNA synthesis was further used in PCR reaction and served as the negative control.

More than thirty different human cancer cell lines were employed to investigate the expression of GnRH receptor by using RT-PCR (a) or by indirect immunofluorescence staining of Western blot assays (b). The results are summarized in Table 1.

TABLE 1

Expression of GnRHR1 in cancer cell lines as detected by RT-PCR[a], Western blot assays[b] and Immunohistochemical staining[c]

| Cell Line | | | Relative GnRHR1 Signal* | | |
|---|---|---|---|---|---|
| Origins | Designation | ATCC No. | (a) | (b) | (c) |
| Breast | MCF7 | HTB-22 | ± | ND | + |
| | MDA-MB-231 | HTB-26 | + | + | + |
| | MDA-435 | | ± | ND | + |
| | T-47D | HTB-133 | ± | ND | + |
| Cervix | C-33A | HTB-31 | + | + | ++ |
| | Hela | | ND | ND | + |
| | SiHa | HTB-35 | + | ND | ND |
| | ME-180 | HTB-33 | + | ND | ++ |
| Colon | HCT 115 | | + | ND | + |
| | HCT 116 | CCL-247 | + | ND | + |
| | HT-29 | HTB-38 | + | ND | + |
| | SW-48 | CCL-231 | ± | ND | + |
| Glioblastoma | HTB-14 | U-87 MG | + | ND | ND |
| Hepatocellular | Hep3B | HB-8064 | + | ND | + |
| | HepG2 | HB-8065 | + | ND | + |
| | Hep-2 | | ± | ND | + |
| Kidney | FS293 | | ND | ND | + |
| Lung | A549 | CCL-185 | + | + | + |
| | Calu-6 | HTB-56 | + | ND | + |
| | H441 | HTB-174 | + | ± | + |
| | MRC-5** | CCL-171 | + | ND | + |
| | WI-38** | CCL-75 | + | ND | ND |
| Lymphoma | HEL 1 | | ± | + | + |
| Leukemia | K-562 | CCL-243 | + | + | + |
| Melanoma | MMAN | | ± | ND | + |
| | MMRU | | + | ND | ND |
| | SK-MEL-3 | HTB-69 | ± | ND | ND |
| Neuroblastoma | SH-SY5Y | CRL-2266 | + | ND | ND |
| Human Ovarian | SK-OV-3 | HTB-77 | ± | + | + |
| | OC-3-VGH | | + | + | + |
| | OVCAR-3 | HTB-161 | ND | + | + |
| Placenta | JEG-3 | HTB-36 | + | ND | ND |
| | Bewo | | ND | ND | + |
| Prostate | DU 145 | HTB-81 | + | ND | + |
| | PC-3 | CRL-1435 | ± | ND | + |
| T-cell Leukemia | Jurkat | TIB-152 | − | ND | ND |

*The strength of the signal in the order of ++ (very strong), + (strong), ± (weak), − (invisible)
**Normal hyperplastic and proliferated fibroblast cell lines derived from fetal lung tissue
ND: not determined Of thirty-three cell lines tested, only Jurkat cells (T-cell leukemia), showed little or no evidence of GnRH receptor mRNA expression by RT-PCR.

Example 1

Generation and Selection of Monoclonal Antibodies Against Human GnRH Receptor

Oligopeptides corresponding to amino acid residues 1-29, 182-193, 195-206 and 293-306 in the extracellular domains of human GnRH receptor were custom synthesized by Gemed Lab, South San Francisco, Calif. and Genescript, NJ, and conjugated separately to keyhole limpet hemocyanin (KLH) by standard methods. These conjugates were used as immunogens to generate monoclonal antibodies as previously described. Lee, G-C. Y., et al., *Am J Reprod Immunol* (2000) 44:170-177.

Several monoclonal antibodies were generated against the synthetic peptide corresponding to positions 1-29 in the extracellular domain of GnRHR. One of the monoclonal antibodies, GHR-106, was selected for further characterization. A murine hybridoma that secretes GHR-106 was deposited at the American Type Culture Collection, Rockville, Md. on Aug. 5, 2009 under the terms of the Budapest Treaty and assigned an ATCC® Patent Deposition Designation of GHR-106 PTA-10252.

The encoding sequences for GHR-106 were obtained from the hybridoma secreting this antibody and the sequences of the variable regions are set forth in FIG. 1.

Example 2

Characterization of GHR-106 Monoclonal Antibody

Microwells coated with synthetic peptide or cancer cells were used to estimate the affinity constant between GHR-106 and GnRH receptor. Following one hour incubation at 37° C. with GHR-106 in microwells, goat anti-mouse IgG labeled with alkaline phosphatase served as the second antibody for signal detection with p-nitrophenylphosphate. As shown in FIG. 2A, GHR-106 showed dose-dependent binding to 1-29 synthetic peptide coated onto microwells. Similar dose-dependent binding was observed between GHR106 and OC-3-VGH cancer cells coated on microwells, as shown in FIG. 2B using the foregoing assay conducted under similar conditions.

Based on the results of these binding assays, the dissociation constant (Kd) was estimated to be $2 \times 10^{-9}$ M.

Figure 3:
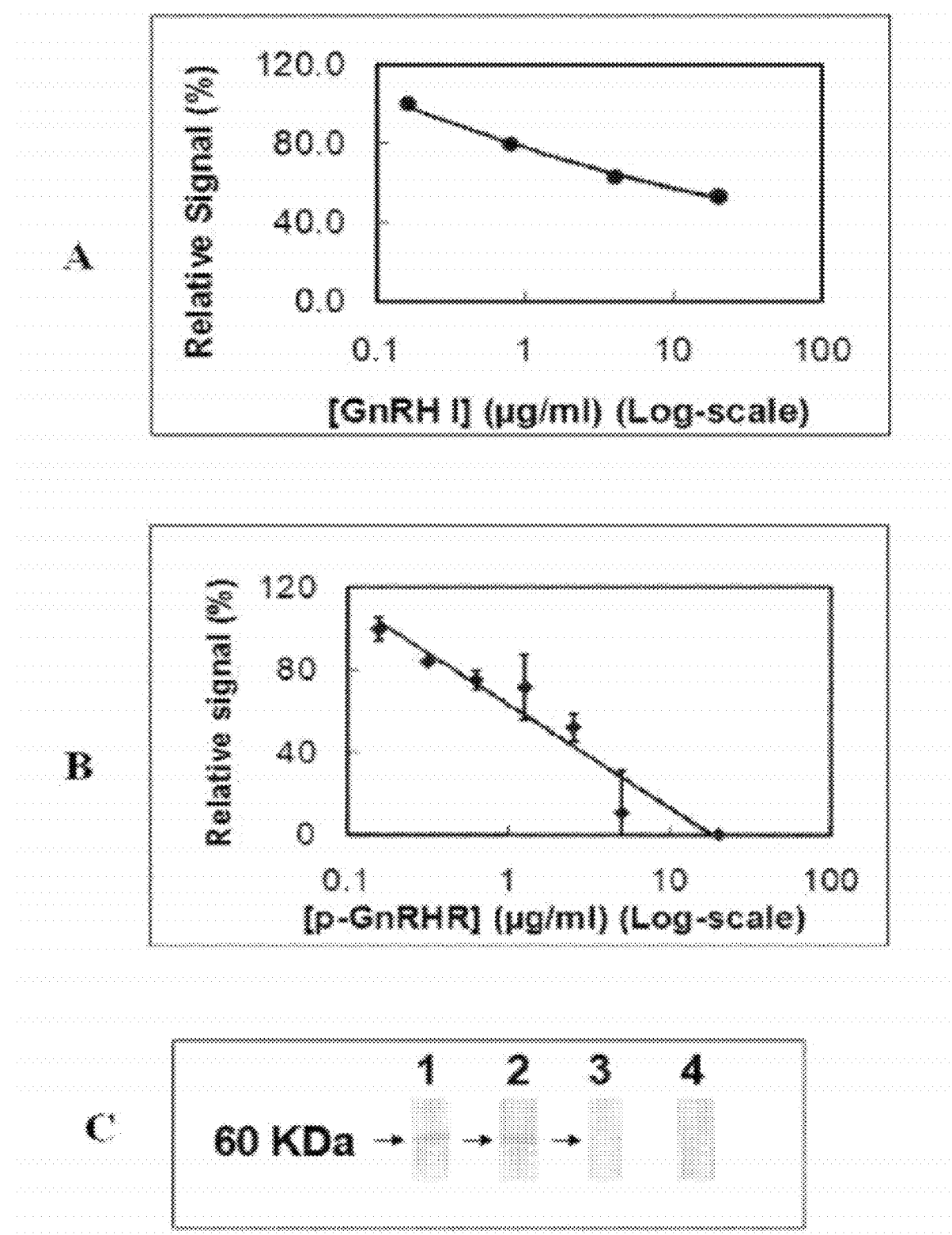
FIGS. 3A and 3B show competition of GnRH (3A) or 1-29 peptide (3B) with GHR-106 for binding to microwells coated with OC-3-VGH cancer cells. The relative signal as percent of the maximum was plotted against the peptide concentrations (in Log scale).
FIG. 3C Western blot assay to reveal the protein band (s) of 60 KDa from OC-3-VGH cancer cell extract recognized by GHR-103 (Lane 1), GHR-106 (Lane 2), and GHR-114 (Lane 3). Normal mouse IgG was used as a negative control (Lane 4).

Using the assay conditions of FIGS. 2A and 2B, GnRH I was shown to inhibit the binding of GHR-106 to OC-3-GH cancer cells coated on microwells using 2 μg/ml GHR-106. The decrease in relative signal intensity of antibody binding to cancer cells with increasing GnRH concentrations ranging from 0.1 to 10 μg/ml is shown in FIG. 3A. Similarly, 1-29 synthetic peptide was shown to inhibit GHR-106 binding to immobilized cancer cells, as shown in FIG. 3B.

Western blot assay was performed with GHR-106 using alkaline phosphatase-labeled goat anti-mouse IgG as the detecting probe. One single protein band from OC-3-VGH ovarian cancer cell extract was observed with molecular weight of approximately 60 KDa, which is identical to that for the human GnRH receptor.

Example 3

Induction of Apoptosis of Cancer Cells by GnRH and GHR-106

A. TUNEL Assay

In order to investigate the anti-proliferative effects (or apoptosis) of GHR-106 on cancer cells, In Situ Cell Death Detection Kit, POD (Roch, Canada) was employed for detection and quantitation of apoptosis at a single cell level. Briefly OC-3-VGH ovarian cancer cells were cultured in RPMI-1640 medium at 37° C. in a $CO_2$ (5%) incubator for two to three days until all cancer cells are attached to microwells. Following removal of cell culture medium, fresh serum-free medium was added for additional 3 hours incubation in $CO_2$ incubator.

After the serum-free starving period, the cells were incubated in fresh medium containing 10% fetal calf serum, GnRH or GHR-106 of known concentrations was added for co-incubation of 24 to 72 hours. As the negative control, normal mouse IgG of the same concentration was used for the same incubation period.

At the end of incubation, the attached cells were removed from tissue culture wells by appropriate cell detachment solution (Accutase, Sigma). Apoptosis of treated cancer cells was quantitatively determined by TUNEL assay with the instructions provided by Cell Death Detection Kit, POD (Roche Canada). Percent increases of cells with apoptosis after treatments with either GnRH I or GHR-106 was obtained by subtracting spontaneous apoptosis from the negative control.

Figure 4:
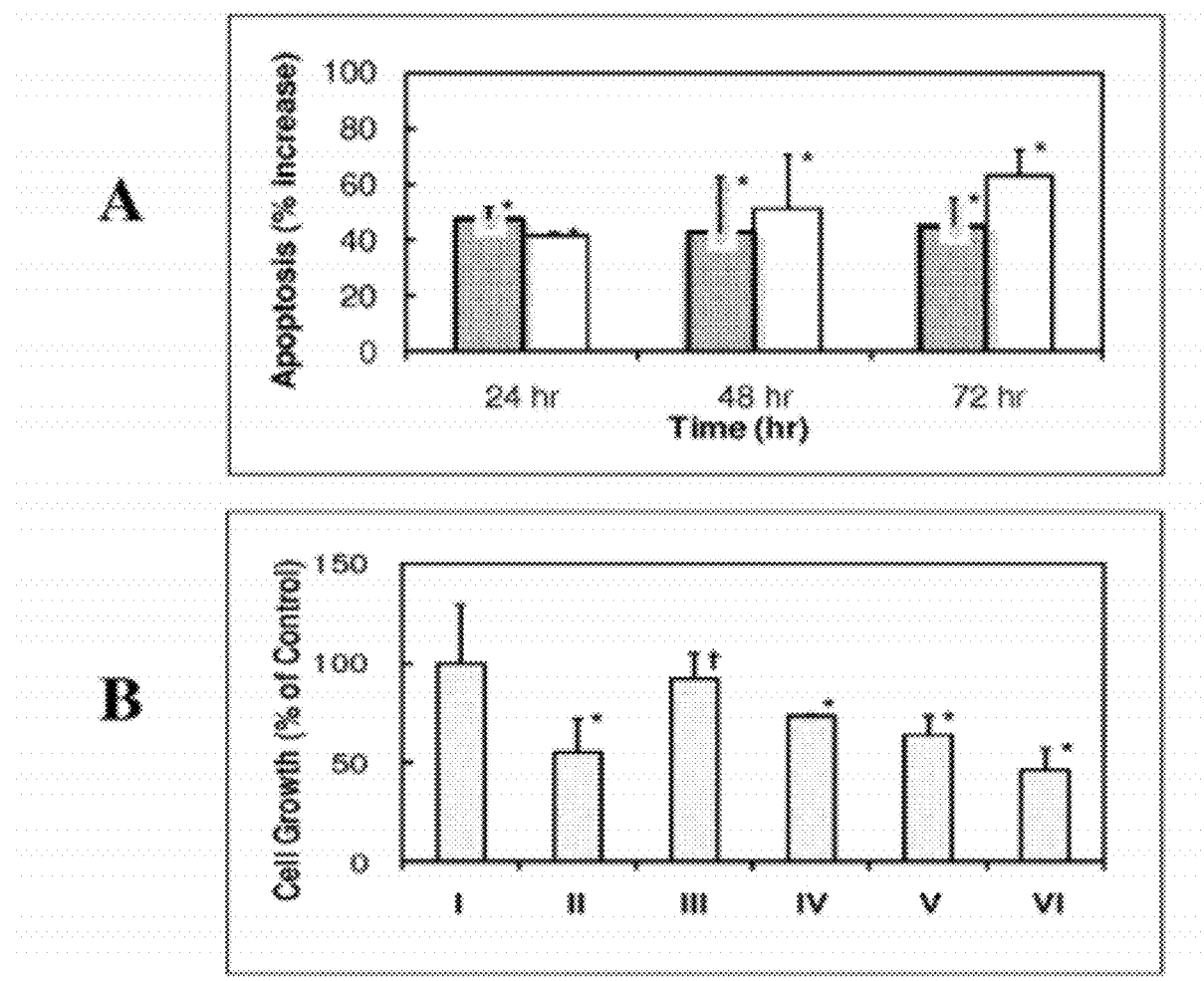
FIG. 4A shows percent increases in apoptosis of cancer cells in response to treatments of OC-3-VGH cancer cells with GHR-106 monoclonal antibody (grey) or GnRH (white) for 24, 48 and 72 hours, using the TUNEL assay.
FIG. 4B shows similar results using the MTT assay. I: Negative control; II: GnRH I (0.1 μg/ml) (p<0.05); III: Antide (0.1 μg/ml) (p>0.05); IV: Antide (0.2 μg/ml) (p<0.05); V: GHR-106 (10 μg/ml) (p<0.05); and VI: GHR-106 (20 μg/ml) Mab, respectively for 48 hrs on the cultured cancer cells.

As shown in FIG. 4A, 40% to 65% increase in apoptosis of treated cancer cells was detected upon the treatment with either 10 μg/ml of GHR-106 or 0.1 μg/ml of GnRH I. Increase in induction of cellular apoptosis with GHR-106 was observed over 24 to 72 hrs as compared to the negative control (p<0.05). Apoptotic induction with GnRH I treatments increased significantly from 24 to 72 hrs of incubation time (p<0.05).

Table 2 shows percent increases in apoptosis of cancer cells in response to treatments of different cancer cells other than OC-3-VGH with GHR-106 monoclonal antibody for 24 hours, using the TUNEL assay. RP215 and Goat anti-human IgG were used as positive control.

TABLE 2

Apoptosis assay
24-hour Treatment

| Cell Line | Antibody | Dosage (μg/mL) | % Apoptosis (Negative Control*) |
|---|---|---|---|
| A549 | RP215 | 10 | 30 ± 9 (11 ± 5)+ |
| | | 20 | 36 ± 12 (17 ± 3)+ |
| | GHR106 | 10 | 34 ± 10 (11 ± 5)+ |
| | | 20 | 46 ± 11 (17 ± 3)+ |
| DU-145 | RP215 | 10 | 32 ± 7 (12 ± 3)+ |
| | | 20 | 43 ± 4 (19 ± 15)− |
| | GHR106 | 10 | 32 ± 2 (12 ± 3)+ |
| | | 20 | 32 ± 5 (19 ± 15)− |
| | Goat anti Human IgG | 10 | 46 ± 9 (12 ± 3)+ |
| MDA-MB-435S | RP215 | 20 | 37 ± 8 (6 ± 1)+ |
| | GHR106 | 10 | 31 ± 4 (7 ± 2)+ |
| | | 20 | 45 ± 11 (6 ± 1)+ |
| | Goat anti Human IgG | 10 | 44 ± 4 (7 ± 2)+ |

B. MTT Assay

Anti-proliferative effects of GnRH and GHR-106 monoclonal antibody on the growth of cultured cancer cells were also studied by MTT assay. An MTT assay was performed on cancer cells on a 24-well plate, as described by Choi, J-H, et al., *Endocrine-Related Cancer* (2006) 13:641-651.

$1 \times 10^4$ Cells were dispensed into each well and cultured for 48 hours. Following removal of cultured media, fresh medium containing GnRH (0.1 μg/ml) or GHR-106 (10 μg/ml) was added to each well for additional 48 hours incubation. After the culture medium was removed, 200 μl of MTT (3-(4,5-dimethylthiazol-2-yl)-2,5-diphenyltetrazoliumbromide) (2.5 mg/ml in PBS, Sigma) was added to each well. After 5 hours of incubation with MTT at 37° C. in a 5% $CO_2$ incubator, the supernatant was removed, and 200 μl of dimethylsulfoxide (DMSO) was added to each well, and shaking at 150 rpm for 5 min. Absorbance at 560 nm was determined spectrophotometrically. The negative control containing cells without any antibody treatment served as the negative control.

The results of this assay are presented in FIG. 4B. MTT assay showed the anti-proliferative effects to cultured OC-3-VGH ovarian cancer cells upon incubation with GnRH (0.1 μg/ml), Antide (0.1 μg/ml, 0.2 μg/ml), and GHR-106 (10 μg/ml, 20 μg/ml) monoclonal antibody, respectively for 48 hrs. Relative Absorbance at 560 nm was normalized with negative control (NC) without treatment. Both GnRH and GHR-106 significantly inhibit the growth of cultured cancer cells upon incubation for 48 hours with the hormone or with monoclonal antibody (p<0.05). Dose dependence was shown for GHR-106, Antide, a GnRH antagonist, was also shown to induce apoptosis, although to a much lesser extent.

Example 4

Effect of Antibody or Hormone Treatments on the mRNA Expression of Selected Ribosomal Proteins and EGF Receptor Four ribosomal proteins (P0, P1, P2 and L37) were selected for semi-quantitative analysis of mRNA expression. Expression of mRNA of GAPDH gene was used as the internal control. Primers for amplification were as follows:

A housekeeping gene, glyceraldehyde-3-phosphate dehydrogenase (GAPDH) was amplified to check the functional integrity of cDNA and used as internal control by using 5'-GAAATCCCATCACCATCTTCC-3' (sense) (SEQ ID NO:20) and 5'-CCAGGGGTCTTACTCCTTGG-3' (antisense) (SEQ ID NO:21) as primers (805 bp) (11).

```
PO (431 bp):
                                      (SEQ ID NO: 12)
5'-TTGTGTTCACCAAGGAGG-3' (sense)
and
                                      (SEQ ID NO: 13)
5'-GTAGCCAATCTGCAGACAG-3' (antisense),
respectively;
P1 (476 bp):
                                      (SEQ ID NO: 14)
5'-CAAGGTGCTCGGTCCTTC-3' (sense)
and
                                      (SEQ ID NO: 15)
5'-GAACATGTTATAAAAGAGG-3' (antisense);
P2 (386 bp):
                                      (SEQ ID NO: 16)
5'-TCCGCCGCAGACGCCGC-3' (sense)
and
                                      (SEQ ID NO: 17)
5'-TGCAGGGGAGCAGGAATT-3' (antisense);
L37 (340 bp):
                                      (SEQ ID NO: 18)
5'-CAGAAGCGAGATGACGAAGG-3' (sense)
and
                                      (SEQ ID NO: 19)
5'-CCAGAACATTTATTGCATGAC-3' (antisense) (10).
```

RNA extraction, cDNA preparation and PCR amplification were conducted as described above in Preparation A.

Figure 5:
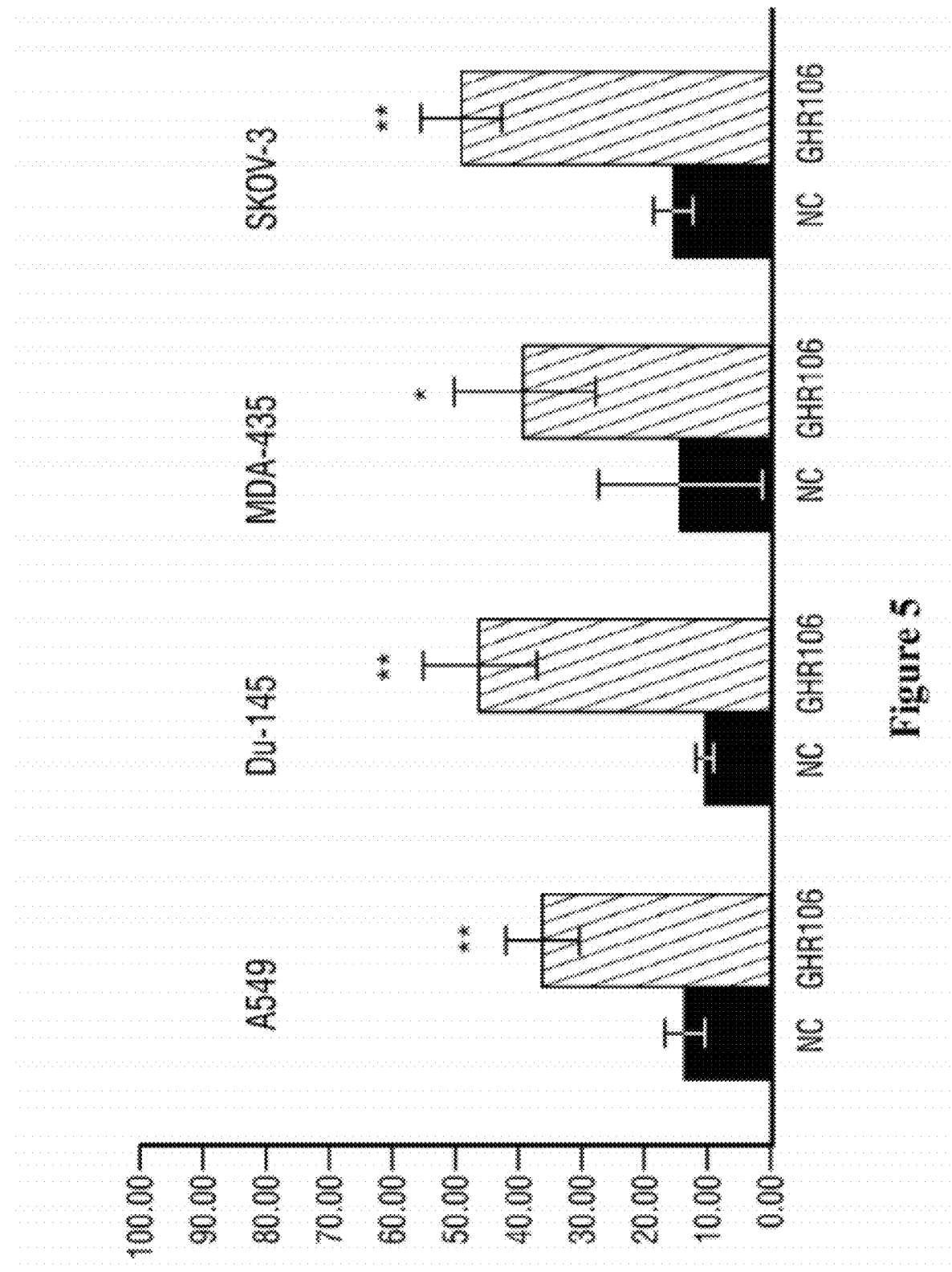
FIG. 5 shows percent apoptosis in response to treatment of A549, DU-145, MDA-435 and SKOV-3 cancer cells with GHR-106 monoclonal antibody (white) for 48 hours. Negative controls are shown in black.

Upon 24-hour treatment with GHR-106, significant decrease in expression of these four ribosomal proteins was clearly observed. The results of the semi-quantitative analysis are presented in FIG. 5 which shows down regulation of mRNA expression of four selected ribosomal proteins (P0, P1, P2 and L37) upon treatment of OC-3-VGH cancer cells with GHR-106 monoclonal antibody (10 µg/ml) (Grey) or GnRH (0.1 µg/ml) (Black) for an incubation period of 24 hours. mRNA expression of GAPDH gene was used as the internal control and treated as 100%. Percent changes in RT-PCR signals which represent levels of P0, P1, P2, and L37 ribosomal proteins are presented with respect to GAPDH (100%) at 0 and 24 hrs. Messenger RNA expression of these genes of cultured cells without GHR-106 treatment served as the internal negative control and those with GnRH treatment served as positive control.

Example 5

Immunohistochemical Staining Studies

Figure 6:
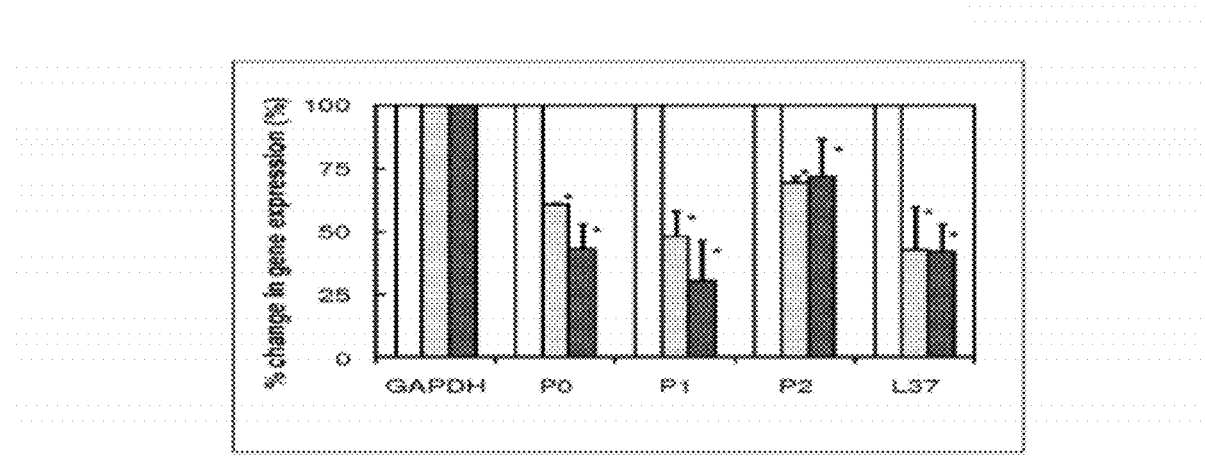
FIG. 6 shows the effect of GHR-106 on down-regulated expression of ribosomal proteins in OC-3-VGH cells.
Figure 7:
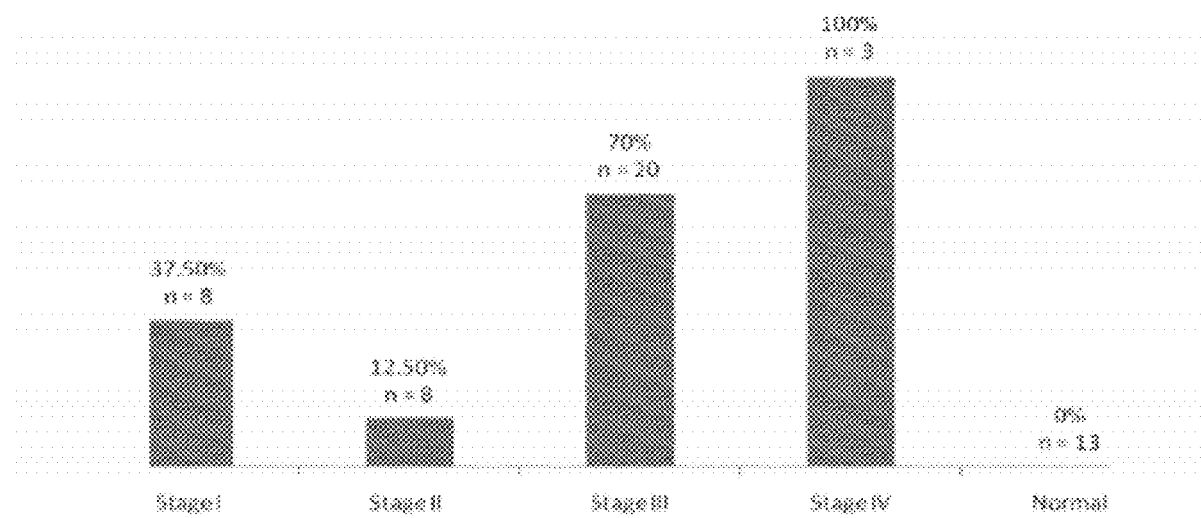
FIG. 7 is a graph showing the degree of immunohistochemical staining (IHC) rates of ovarian tissues obtained from patients diagnosed with different stages of ovarian cancers. Normal ovarian tissues from patients without ovarian cancers were negatively stained in the same procedure.
Figure 8:
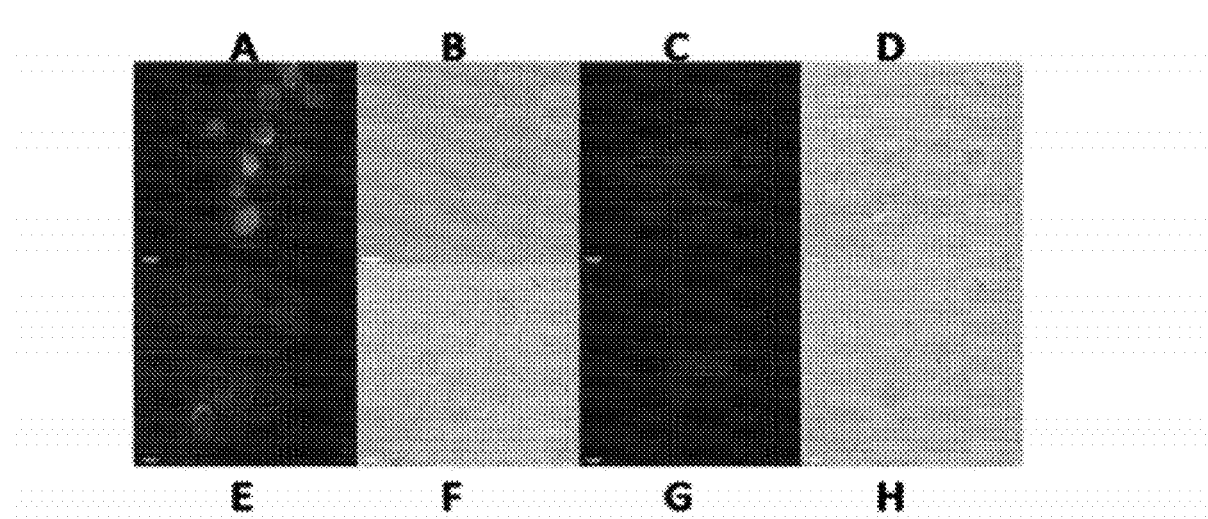
FIG. 8 shows indirect immunofluorescence staining (under UV light) by using GHR-106 to demonstrate the presence of GnRH receptor on the surface of cancer cells, including OC-3-VGH ovarian cancer cell line (A) and C-33A cervical cancer cell line (E). (B) and (F) are the corresponding cells visualized under the visible light, respectively. For the negative control, the corresponding cancer cells were stained with normal mouse IgG of the same concentration as the primary antibody. The results are shown in (C, D) for OC-3-VGH and (G, H) for C-33A, respectively.
Figure 9:
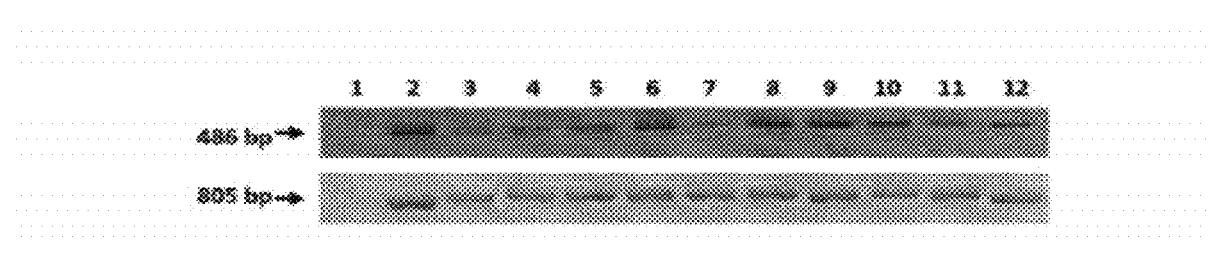
FIG. 9 shows the PCR products (486 bp) using GnRHR1 primers to indicate the expression of GnRHR1 chain in cancer cell lines. Lane 1: Negative control showed no band; Lane 2: Calu6; Lane 3: HCT 115; Lane 4: H441; Lane 5: Hep3B; Lane 6: HT-29; Lane 7: SW-48; Lane 8: SK-OV-3; Lane 9: MMRU; Lane 10: MRC-5; Lane 11: MCF7; and Lane 12: OC-3-VGH. Expression of housekeeping gene GAPDH (805 bp) is also presented to check the integrity of cDNA from each cancer cell line and to normalize the cDNA concentrations.

Standard immunohistochemical (IHC) staining studies were performed on cancer tissues from 39 patients diagnosed with ovarian cancers at different stages using GHR-106. As shown in FIG. 6, the positive staining rates depend on the stages of ovarian cancers. At stage I, about 40% of cases are positive, whereas at the advanced stages (i.e., stages III and IV), the positive rates are 73 to 100%. In contrast, 13 normal controls showed no staining.

The invention claimed is:

1. Recombinant host cells or immortalized cells that produce an mAb or fragment thereof that reacts specifically with an epitope present in amino acid residues 1-29 (SEQ ID NO:7) of the extracellular domain of the human GnRH receptor, and that binds to the GnRH receptor with a dissociation constant ($K_D$) of less than or equal to $10^{-7}$ M, and that competes with GnRH for binding to the receptor.

2. The recombinant host cells of claim 1 wherein said mAb or fragment comprises:

a CDR1 region of the heavy chain having the amino acid sequence RYSVH (SEQ ID NO:1); and a CDR2 region of the heavy chain having the amino acid sequence MIWGGGSTDYNSALKS (SEQ ID NO:2); and a CDR3 region of the heavy chain having the amino acid sequence GNDGYYSFAY (SEQ ID NO:3); and a CDR1 region of the light chain having the amino acid sequence KSSQSLLNSRTRKNYLA (SEQ ID NO:4); and a CDR2 region of the light chain having the amino acid sequence WASTRES (SEQ ID NO:5); and a CDR3 region of light chain having the amino acid sequence KQSYNLYT (SEQ ID NO:6).

3. The recombinant host cells of claim 1 wherein said fragment is an F(ab')$_2$, Fab, Fv, or scFv fragment.

4. The recombinant host cells of claim 1 which are mammalian cells, microbial cells, insect cells or plant cells.

5. A method to produce an mAb or fragment, which method comprises culturing the cells of claim 1 and recovering said mAb or fragment.

6. A method to produce an mAb or fragment, which method comprises culturing the cells of claim 2 and recovering said mAb or fragment.

7. The method of claim 6 wherein the fragment is an F(ab')$_2$, Fab, Fv, or scFv fragment.

8. The method of claim 6 wherein said cells are mammalian cells, microbial cells, insect cells or plant cells.

\* \* \* \* \*